United States Patent
Ono et al.

(10) Patent No.: US 6,640,623 B2
(45) Date of Patent: Nov. 4, 2003

(54) ROAD SURFACE STATE ESTIMATING DEVICE

(75) Inventors: Eiichi Ono, Aichi-gun (JP); Takaji Umeno, Aichi-gun (JP); Masaru Sugai, Aichi-gun (JP); Akira Tanaka, Kodaira (JP); Yoshiyuki Yasui, Nagoya (JP); Mamoru Sawada, Yokkaichi (JP)

(73) Assignee: Toyota Jidosha Kabushiki Kaisha, Toyota (JP)

( * ) Notice: Subject to any disclaimer, the term of this patent is extended or adjusted under 35 U.S.C. 154(b) by 0 days.

(21) Appl. No.: 09/976,163

(22) Filed: Oct. 15, 2001

(65) Prior Publication Data

US 2002/0059824 A1 May 23, 2002

(30) Foreign Application Priority Data

Oct. 16, 2000 (JP) ........................................ 2000-315836

(51) Int. Cl.$^7$ ............................................... E01C 23/00
(52) U.S. Cl. ......................................................... 73/146
(58) Field of Search .............................. 73/146, 146.2, 73/146.3, 146.5, 146.8; 340/442–448; 152/415, 419

(56) References Cited

U.S. PATENT DOCUMENTS 5,719,565 A * 2/1998 Tsuno et al. ................. 340/905
6,264,292 B1 * 7/2001 Umeno et al. ............... 303/196

FOREIGN PATENT DOCUMENTS

| DE | 195 43 928 C2 | 5/1997 |
| DE | 195 45 013 A1 | 6/1997 |
| DE | 196 02 170 A1 | 7/1997 |
| JP | A 11-78843 | 3/1999 |
| JP | A 2000-118375 | 4/2000 |

* cited by examiner

Primary Examiner—Edward Lefkowitz
Assistant Examiner—C. Dickens
(74) Attorney, Agent, or Firm—Oliff & Berridge, PLC

(57) ABSTRACT

In order to estimate a braking force gradient in a low slip region including a steady travelling region, there is provided a device comprising a wheel speed sensor for detecting a wheel speed in a predetermined sampling period and outputting time series data of the wheel speed as a wheel speed signal, a break point frequency estimating section for estimating a break point frequency in a gain diagram that represents a frequency response of a first order lag model that approximates a transmission characteristics from road surface disturbances to wheel speed, and a braking force gradient estimating section for estimating a braking force gradient with respect to the estimated break point frequency on the basis of the map showing a relationship between braking force gradient and break point frequency stored in advance.

13 Claims, 9 Drawing Sheets

FREQUENCY RESPONSE to WHEEL SPEED from ROAD SURFACE DISTURBANCES
(BRAKING FORCE GRADIENT = 300 TO 10,000 Ns/m)

ROAD SURFACE DISTURBANCES

FREQUENCY RESPONSE to WHEEL SPEED from
ROAD SURFACE DISTURBANCES
(BRAKING FORCE GRADIENT = 300 TO 10,000 Ns/m)

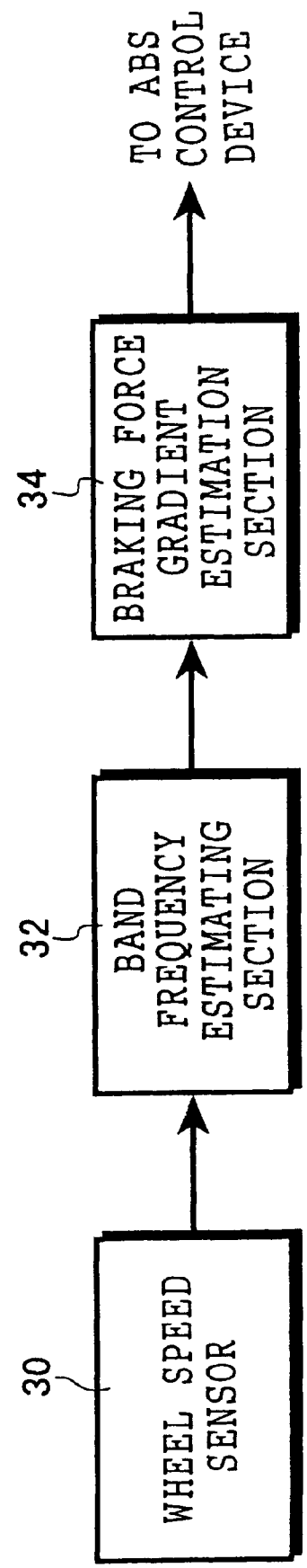
F I G. 4

F I G. 1 0
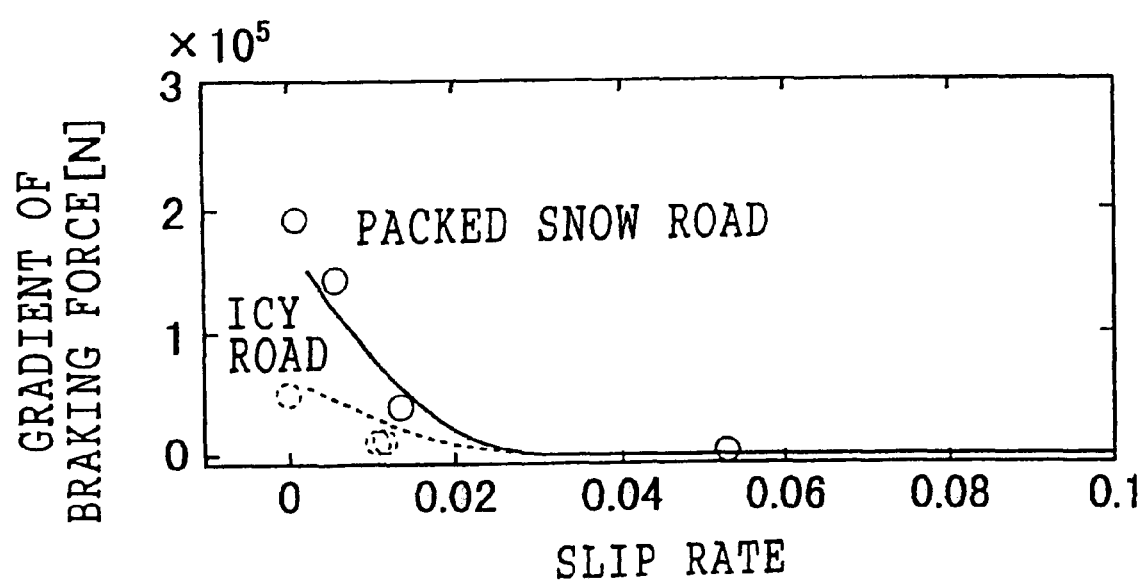

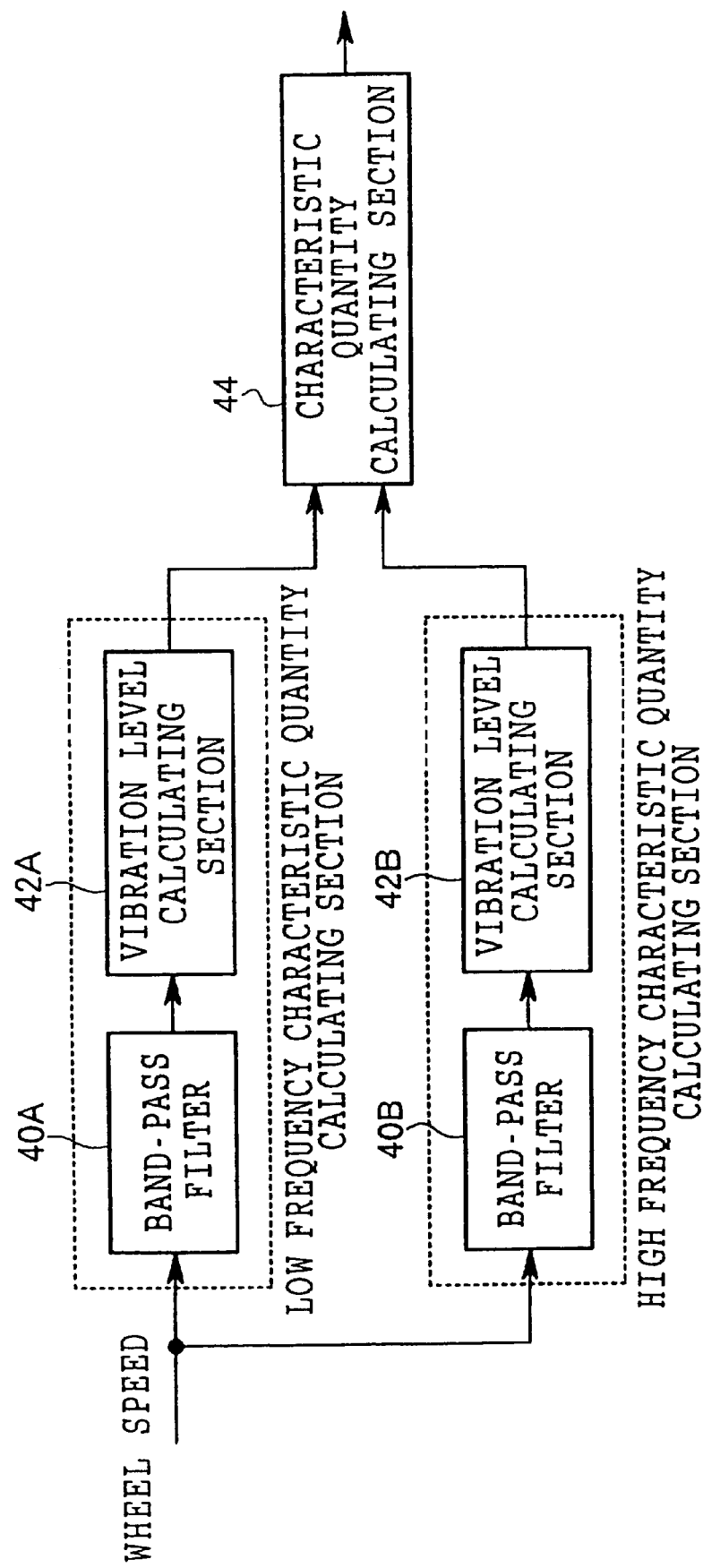

ROAD SURFACE STATE ESTIMATING DEVICE

BACKGROUND OF THE INVENTION

1. Field of the invention

The present invention relates to a road surface state estimating device and, more particularly, to a road surface state estimating device (a device for estimating the state of a road surface) that estimates a physical quantity representing a road surface state such as a braking force gradient and a driving force gradient in a low slip region including a steady traveling (running) region.

2. Description of the Related Art

Japanese Patent Application Laid-Open (JP-A) No. 2000-118375 discloses an ABS device for estimating a braking torque gradient (obtained by a braking force gradient being multiplied with a square of a wheel effective radius) from a wheel speed signal, and maximizing braking force by controlling the estimated braking torque gradient to coincide with a target value near zero. In this device, the braking torque gradient is estimated on the basis of a wheel deceleration motion model represented by the following Equation (1), whereby the braking torque gradient, therefore, the braking force gradient can be accurately estimated in a limit braking region where a wheel deceleration motion is dominant.

$$\dot{v}_w = -\frac{kR_c^2}{J}v_w + w \quad (1)$$

where $v_w$ represents a wheel speed (m/s); w represents a road surface disturbance; k represents a braking force gradient (Ns/m); $R_C$ represents an effective radius of the tire (m); and J represents moment of inertia of a vehicle.

However, in a low slip region where the braking force gradient is relatively large, the wheel deceleration motion is affected by a suspension longitudinal resonance, which is a resonance generated at near 15 Hz, and a tire rotation resonance, which is a resonance generated at near 40 Hz. Therefore, there is a problem in that it is not possible to accurately estimate the braking force gradient in the low slip region by the technique in which the braking torque gradient is estimated on the basis of the Equation (1).

Japanese Patent Application Laid-Open (JP-A) No. 11-78843 discloses a wheel state estimating device, wherein a braking force gradient is estimated on the basis of a tire rotation vibration model. By noting that resonance characteristics of the tire rotation vibration become sharper as the braking force gradient becomes larger, a damping coefficient of the tire rotation vibration is identified to estimate the braking force gradient.

However, in a case of braking in which the braking force gradient becomes small, because wheel deceleration motion becomes dominant, tire rotation vibration is not generated. Therefore, in the prior art described above, there is a problem in that the braking force gradient cannot be estimated in a case of braking in which tire rotation vibration is not generated.

SUMMARY OF THE PRESENT INVENTION

The present invention has been conceived to solve the above problem. It is an object of the present invention to provide a road surface state estimating device which estimates a physical quantity representing a road surface state such as a braking force gradient, a driving force gradient and a road surface μ gradient in a low slip region including a steady travelling (running) region.

Principles of the present invention will now be described. As shown in FIG. 1, a wheel resonance system can be represented by a dynamic model in which torsional spring elements 14 and 16 of a tire, having respective spring constants K1 and K2, are interposed between a rim 10 and a belt 12 and in which a suspension element, in which a spring element 18 having a spring constant K3 is connected in parallel with a damper 20, is interposed between the rim 10 and a vehicle body. In this model, a disturbance from the road surface (road surface disturbance) is transmitted from the belt 12 through the spring elements 14 and 16 to the rim 10, to affect a wheel speed ω, and is transmitted to the vehicle body through the suspension element.

Description will now be given of relation between the braking force gradient and a wheel speed frequency characteristic quantity representing following frequency of transmission characteristics from a road surface disturbance to the wheel speed, using a fifth order full wheel model, in which a first order wheel decelerating motion, second order longitudinal direction suspension resonance, and second order tire rotation resonance are integrated. The braking force gradient is represented, as shown in FIG. 2, by a gradient of a tangent of a curve representing a relationship between a braking force and a slip speed (or slip rate).

FIG. 3 is a gain diagram showing frequency responses from a road surface disturbance to the wheel speed for ranges from a limit braking range to a low slip range where there is some margin for tire characteristics (i.e., for ranges from a range at which the braking force gradient is 300 Ns/m to a range at which the braking force gradient is 10000 Ns/m). That is, the diagram shows the relationship between frequency and gain of amplitude of the wheel speed with respect to amplitude of the road surface disturbance.

The wheel speed frequency characteristics in FIG. 3 indicate that, for the range where the braking force gradient is relatively small, such as near the limit of friction force between a tire and a road, the gain is large in a low frequency range and is small in a high frequency range. Namely, for the range where the braking force gradient is relatively small, the wheel speed frequency characteristic quantity, which represents a difference between the gain in the low frequency range and the gain in the high frequency range, is large.

In contrast, the gain in the low frequency range for the range where the braking force gradient is relatively large, such as a steady traveling region, is much smaller compared to that for the range where the braking force gradient is relatively small, in the wheel speed frequency characteristics. Further, in the high frequency range, the gain for the range where the braking force gradient is relatively large is not much smaller than the gain for the range where the braking force gradient is relatively small due to the influence of rotational resonance of the tire (near 40 Hz) being generated. Therefore, for the range where the braking force gradient is relatively large, the wheel speed frequency characteristic quantity is small. Also, a wheel speed frequency characteristic quantity, which represents a difference between a vibration level of a wheel speed signal in the low frequency range and a vibration level of a wheel speed signal in the high frequency range, changes similarly to the wheel speed frequency characteristic quantity which represents the difference between the low frequency range gain and the high frequency range gain.

It is apparent from the above that the wheel speed frequency characteristic quantity which represents the difference between the low frequency range gain and the high frequency range gain, or the wheel speed frequency characteristic quantity which represents the difference between the wheel speed signal vibration level in the low frequency range and the wheel speed signal vibration level in the high frequency range, decreases as the braking force gradient increases. Utilizing this characteristic, the braking force gradient can be estimated from the wheel speed frequency characteristic quantity.

Referring to the frequency band near 40 Hz in FIG. 3 at which rotational resonance of the tire occurs, the greater the braking force gradient, the sharper the peak waveform of rotational resonance of the tire. Further, as the braking force gradient becomes greater, the overall frequency characteristics of the peak waveform move to a higher frequency range.

Namely, if the wheel characteristics is approximated to a first-order lag model, it can be understood that a break point frequency becomes higher as the braking force gradient becomes greater, as shown in FIG. 6. It is therefore possible to estimate the braking force gradient from the wheel speed frequency characteristic quantity which represents the following frequency of transmission characteristics from the road disturbance to the wheel speed, by approximating the wheel characteristics to the first-order lag model and estimating the break point frequency (as the wheel speed frequency characteristic quantity), which is a frequency at which the gain changes from a value in a predetermined range to a value out of the predetermined range. Lag models of the second and third orders and the like have characteristics substantially similar to those of the first-order lag model. Therefore, it is possible to estimate a braking force gradient from the value of the wheel speed frequency characteristic quantity, by approximating wheel characteristics to the lower order lag model and estimating the wheel speed frequency characteristic quantity.

The braking force gradient when a braking force is applied to the tire and a driving force gradient when a driving force is applied to the tire are both physical quantities representing slipperiness between the tire and the road surface. Also, the gradient of braking force and the gradient of driving force are physical quantities equivalent to the $\mu$-gradient of the road surface, which represents tire grip state. Accordingly, any one of the braking force gradient, which is a gradient of a tangent of a curve that represents a relationship between a slip rate (or, a slip speed) and a braking force, the driving force gradient, which is a gradient of a tangent of a curve that represents a relationship between a slip rate (or, a slip speed) and a driving force, and a $\mu$-gradient of the road surface, which is a gradient of a tangent of a curve that represents a relationship between a slip rate (or, a slip speed) and a road surface $\mu$, can be estimated as a physical quantity representing slipperiness between the tire and the road surface.

The present invention has been conceived based on the above-described principle. A first aspect of the present invention comprises: a wheel speed sensor for detecting a wheel speed and outputting a wheel speed signal; a wheel speed frequency characteristic quantity estimating section for estimating a wheel speed frequency characteristic quantity which represents a following frequency of a transmission characteristics from a road disturbance to the wheel speed on the basis of the wheel speed signal; and a physical quantity estimating section for estimating a physical quantity which represents a road state, from the estimated wheel speed frequency characteristic quantity.

A second aspect of the present invention comprises: a wheel speed sensor for detecting a wheel speed and outputting a wheel speed signal; a wheel speed frequency characteristic quantity estimating section for estimating a wheel speed frequency characteristic quantity which represents a difference between a characteristic quantity in a low frequency region and a characteristic quantity in a high frequency region which is higher than the low frequency region in a gain diagram representing a frequency response of a transmission characteristics from a road surface disturbance to the wheel speed on the basis of the wheel speed signal; and a physical quantity estimating section for estimating a physical quantity which represents a road state, from the estimated wheel speed frequency characteristic quantity.

A third aspect of the present invention comprises: a wheel speed sensor for detecting a wheel speed and outputting a wheel speed signal; a wheel speed frequency characteristic quantity estimating section for estimating a wheel speed frequency characteristic quantity which represents a following frequency of a transmission characteristics from a road disturbance to the wheel speed on the basis of the wheel speed signal; and a physical quantity estimating section for estimating a physical quantity which represents a road state, from the estimated wheel speed frequency characteristic quantity. In the third aspect of the present invention, the wheel speed frequency characteristic quantity represents, in a transmission characteristics which is from a road surface disturbance to the wheel speed approximated to a low order model, a break point frequency which is a frequency, at which gain changes from a value in a predetermined range to a value out of the predetermined range, in a gain diagram representing a frequency response of the approximated low order model, on the basis of the wheel speed signal.

A fourth aspect of the present invention comprises: a wheel speed sensor for detecting a wheel speed and outputting a wheel speed signal; a wheel speed frequency characteristic quantity estimating section for estimating a physical quantity as a wheel speed frequency characteristic quantity, for each of a plurality of frequency regions which are divided in a gain diagram representing a frequency response of a transmission characteristics from a road surface disturbance to the wheel speed on the basis of the wheel speed signal; and a physical quantity estimating section for estimating a physical quantity which represents a road state, from the plurality of the estimated wheel speed frequency characteristic quantities.

The gain diagram is a diagram which represents the relationship between a frequency and a gain represented by a ratio of an amplitude of an output (an amplitude of time series data of a wheel speed) with respect to an amplitude of an input (an amplitude of road surface disturbance). A sensor that detects wheel speed in a predetermined sampling period and outputs time series data of the wheel speed can be used as the wheel speed sensor.

In the third aspect of the present invention, as the low order model, a first order lag model, a first order lag model or the like can be used, but the first order lag model is preferable.

In the each of the aspects of the present invention, taking advantage of the fact that overall frequency characteristics (waveform) in a frequency band near 40 Hz, in which a tire rotation resonance is generated, move to a higher frequency as the braking force gradient becomes larger, a physical quantity representing slipperiness between the tire and the road surface is estimated as a physical quantity representing the road surface state. Accordingly, a physical quantity representing the state of the road surface in a low slip region including a steady travelling (running) region can be estimated.

BRIEF DESCRIPTION OF THE DRAWINGS

FIG. 4 is a block diagram showing a first embodiment of the present invention.

FIG. 10 is a diagram for comparing estimated values and true values of braking force gradient during forward braking.

FIG. 11 is a block diagram showing a wheel speed frequency characteristic quantity estimating section of a second embodiment of the present invention.

DETAILED DESCRIPTION OF PREFERRED EMBODIMENTS

Preferred embodiments of the present invention will now be described. In a first embodiment of the present invention, a transmission characteristics from road surface disturbances to wheel speed is approximated to a first-order lag model, a break point frequency (band frequency) is estimated from frequency response of the first-order lag model on the basis of time series data of the wheel speed, and a braking force gradient is estimated from the estimated break point frequency.

As shown in FIG. 4, the present embodiment comprises a wheel speed sensor 30, a break point frequency estimating section 32 and a braking force gradient estimating section 34. The wheel speed sensor 30 is for detecting a wheel speed in a predetermined sampling period and outputting time series data of the wheel speed as a wheel speed signal. The break point frequency estimating section 32 is for estimating a break point frequency (a wheel speed frequency characteristic quantity) which is a frequency at which, in a gain diagram that represents a frequency response of a lower order model that approximates a transmission characteristics from road surface disturbances to wheel speed, gain changes from a constant value (a value in a predetermined range to a value out of the predetermined range). The braking force gradient estimating section 34 is for estimating a braking force gradient with respect to the estimated break point frequency on the basis of the map showing a relationship between braking force gradient and break point frequency stored in advance.

In the present embodiment, the braking force gradient estimating section 34 can be connected to an ABS control section for calculating an operation signal for ABS controlling for each wheel on the basis of the braking force gradient estimated by the braking force gradient estimating section 34 and an ABS control valve for operating a braking pressure for each wheel on the basis of the operation signal calculated by the ABS control section so as to perform ABS control.

In FIG. 4, a structure is shown for single wheel. However, for a vehicle having a plurality of wheels such as a four-wheel vehicle, the structure shown in FIG. 4 is provided for each of the wheels.

The break point frequency estimating section of the present embodiment identifies a break point frequency of a first-order lag model using a least squares method with an assumption that a white disturbance, that is, a disturbance including all frequencies, is input to the tire from the road.

Figure 1:
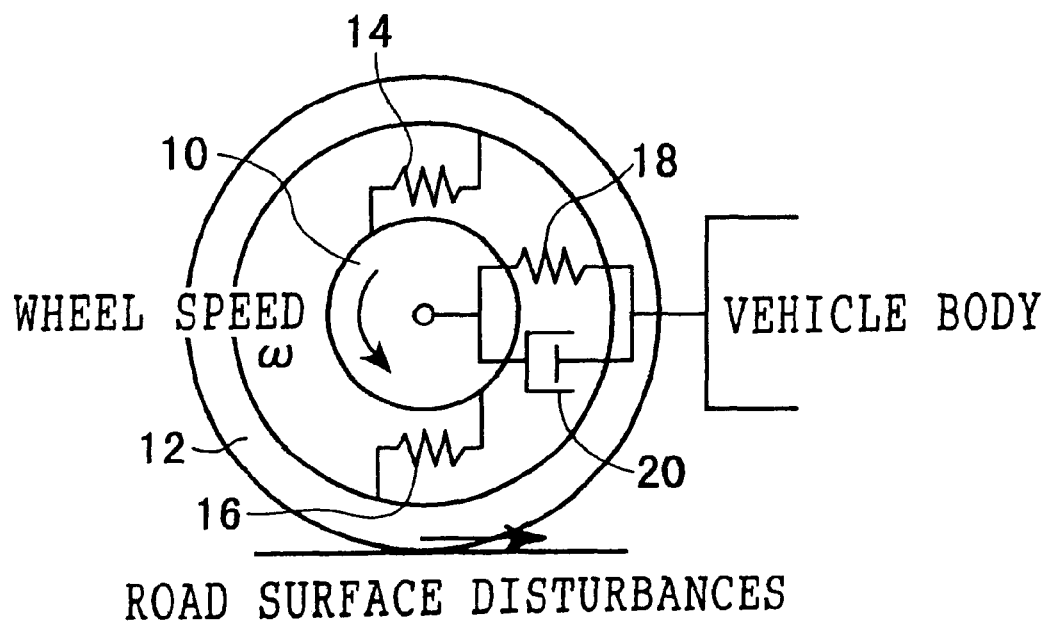
FIG. 1 is a block diagram showing a dynamic model of wheel resonance system of the present invention.
Figure 2:
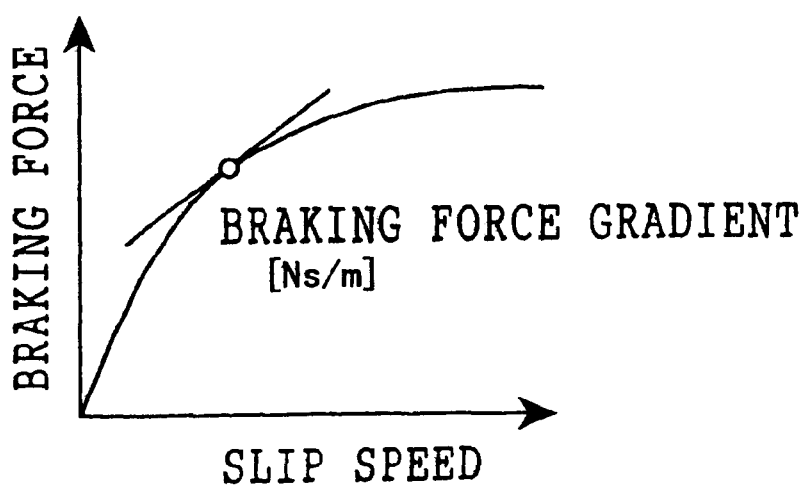
FIG. 2 is a diagram showing relationship between braking force and slip speed.
Figure 5:
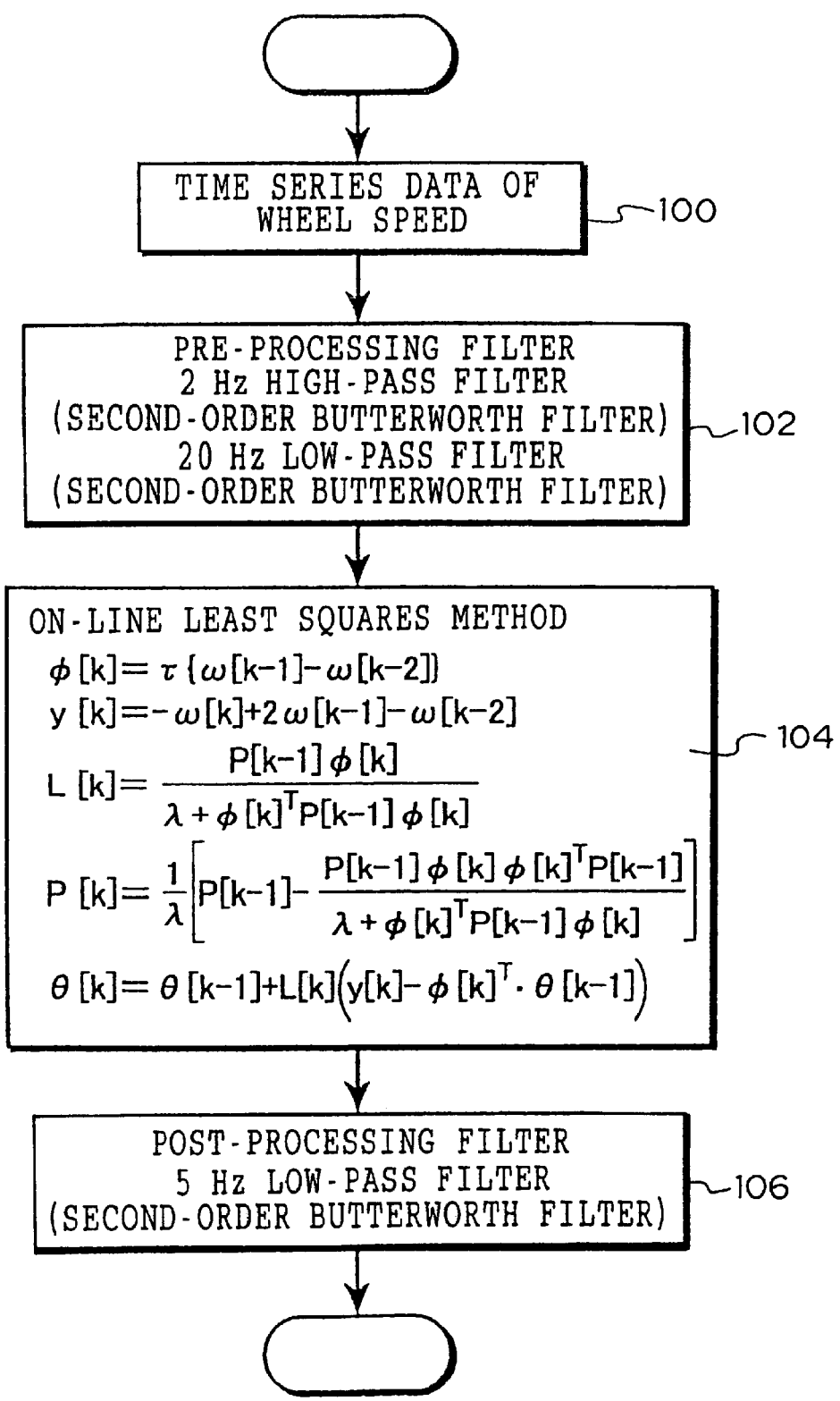
FIG. 5 is a flow chart showing algorithm for estimating a break point frequency in the first embodiment of the present invention.
Figure 6:
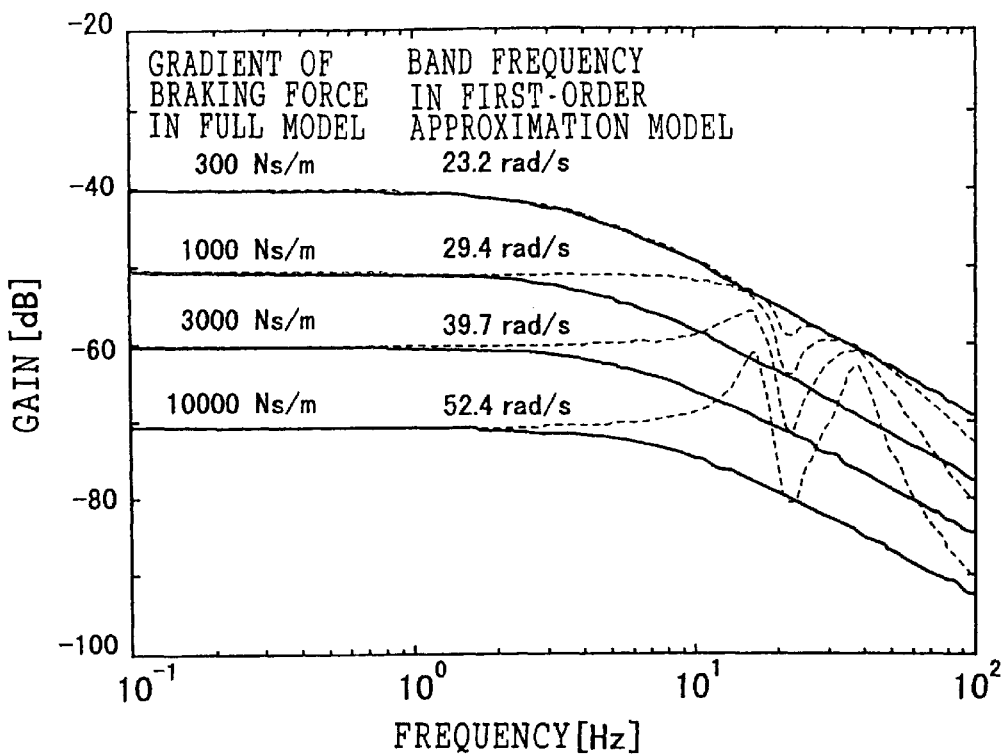
FIG. 6 is a gain diagram showing frequency responses from road surface disturbances to wheel speed in a first-order lag model.

FIG. 5 shows an algorithm for identifying the break point frequency, and FIG. 6 is a gain diagram of first-order lag model associated with break point frequency identified by the algorithm in FIG. 5 when a white disturbance is applied to the full wheel model of FIG. 1.

First, the algorithm for identifying the break point frequency will be described with reference to FIG. 5. At step 100, data, which is the time series data of the wheel speed detected by the wheel speed sensor 30 with white disturbance added, is acquired and then subjected to a pre-process at step 102 using a second-order Butterworth filter, for example, a filter having a 2 Hz high-pass filter and a 20 Hz low-pass filter. Steady components of acceleration of the wheel can be eliminated by inputting the wheel speed signal to the high-pass filter to perform high-pass filtering, and a smoothing process is performed on the wheel speed signal by the low-pass filtering.

At subsequent step 104, time series data of break point frequency is estimated from the pre-processed time series data of the wheel speed using the on-line least squares method. First, the time series data of the wheel speed which has been detected by the wheel speed sensor 30, on a discrete basis at sampling period τ, has been subjected to the pre-process by the filter at step 102. Therefore, this time series data of the wheel speed is represented by ω[k] (k represents sampling times based on the sampling period τ as a unit and takes values 1, 2, and so on). Then, the following steps 1 and 2 are repeated. Thus, time series data of break point frequency is estimated from the detected time series data of the wheel speed.

[Step 1]

$$\phi[k]=\tau\{\omega[k-1]-\omega[k-2]\} \quad (2)$$

$$y[k]=-\omega[k]+2\omega[k-1]-\omega[k-2] \quad (3)$$

φ[k] in Equation 2 is a value obtained by multiplying the quantity of a change in the wheel speed in one sample period by sample period τ (i.e., a physical quantity associated with a change in the wheel speed), and y[k] (a physical quantity associated with a change in a change in the wheel speed) in Equation 3 is a quantity of change in one sample period of the quantity of change (i.e., ω[k−1]−ω[k−2]−ω[k]−ω[k−1]) in the wheel speed in one sample period (ω[k−1]−ω[k−2], [k]−ω[k−1]).

[Step 2]

$$\theta[k]=\theta[k-1]+L[k](y[k]-[k]-\phi[k]^T\cdot\theta[k-1]) \quad (4)$$

Here, $$L[k] = \frac{P[k-1]\phi[k]}{\lambda + \phi[k]^T P[k-1]\phi[k]} \quad (5)$$

$$P[k] = \frac{1}{\lambda}\left[P[k-1] - \frac{P[k-1]\phi[k]\phi[k]^T P[k-1]}{\lambda + \phi[k]^T P[k-1]\phi[k]}\right] \quad (6)$$

An estimated value θ, i.e., a break point frequency, is estimated from the above recurrence formulae. λ in Equations 5 and 6 represents a forgetting coefficient which indicates the degree of elimination of previous data (for example, λ=0.98), and T represents transposition of a matrix.

θ[k] in Equation 4 is a physical quantity representing history of the physical quantity associated with the change in the wheel speed, i.e., wheel acceleration, and history of the physical quantity associated with the change in the change in wheel speed (the change in wheel acceleration).

While an example of estimation of the break point frequency using the on-line least squares method has been described above, the break point frequency can be estimated using other on-line methods, such as the instrumental variable method and the like.

FIG. 6 shows example of result of estimation of the break point frequency in first-order lag model, estimated as described above. As will be understood from the gain diagram in FIG. 6, each gain of an approximated first-order lag model is identified as a characteristics that passes through steady gain in a full wheel model gain diagram and a gain at an antiresonant point (near 40 Hz) for each braking force gradient other than 300 Ns/m. Suspension longitudinal direction resonance near 15 Hz and resonance characteristics of rotational vibration of the tire near 40 Hz are ignored as a result of use of the lower order model. When a braking force gradient is small (300 Ns/m), no resonance is observed because no antiresonant point is passed in the first-order lag model, which indicates that the vibration characteristics of the first-order lag model and the characteristics of the full wheel model agree with each other well. The reason for this is that a wheel deceleration motion model is dominant in a braking region near the limit, where the braking force gradient is 300 Ns/m or less, because there is less influence of suspension longitudinal direction resonance or resonance of rotational vibration of the tire. It is therefore considered that motion of the wheel can be approximated by the following wheel deceleration motion model in this region near the limit.

$$\dot{v}_w = -\frac{kR_c^2}{J}v_w + w \quad (7)$$

where $v_w$ represents a wheel speed (m/s); w represents a road surface disturbance; k represents a braking force gradient (Ns/m); $R_C$ represents an effective radius of the tire (m); J represents moment of inertia of a vehicle; and a coefficient of a first differentiation of $v_w$ represents the break point frequency.

Equation 7 indicates that the following relationship exists between a break point frequency $\omega_0$ and a braking force gradient in the limit region.

$$\omega_0 = \frac{kR_c^2}{J} \quad (8)$$

Figure 7:
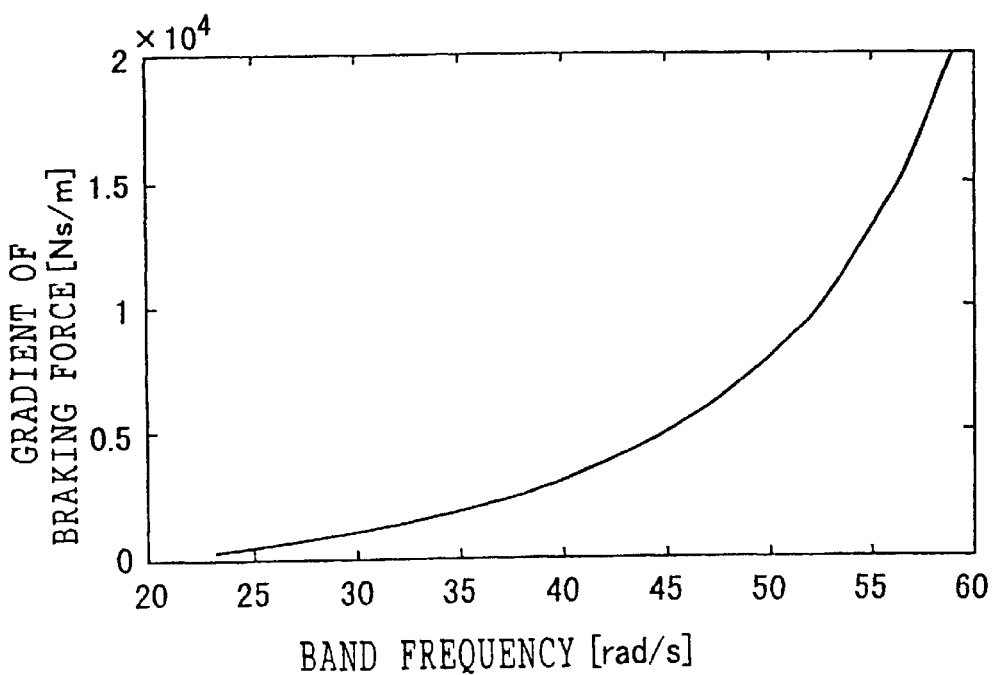
FIG. 7 is a diagram showing a relationship between band frequency and braking force gradient.

In a low slip region, the relationship shown in FIG. 7 can be derived by using a least squares method. FIG. 7 shows the relationship between braking force gradient in the full wheel model and break point frequency identified from wheel speed data with white disturbance added. The unit of the break point frequencies in FIG. 7 are represented [rad/s]. The braking force gradient monotonously increases as the break point frequency increases. In a memory section of the braking force gradient estimating section 34, a relationship, represented by FIG. 7, between braking force gradient and break point frequency, is stored as a map, and, by calculating a braking force gradient corresponding to break point frequency estimated by the break point frequency estimating section 32 on the basis of the wheel speed signal by use of the map. It is therefore possible to estimate the braking force gradient by estimating (identifying) the break point frequency.

Comparing the present embodiment to the technique recited in the JP-A 2000-118375, a braking force gradient is estimated by using the relationship represented by the Equation 8 in the JP-A No. 2000-118375. However, in the present embodiment, braking force gradient is estimated in a region which is expanded to a low slip range including a steady state.

Comparison with Experimental Results

A description is now given of how the relationship for braking with constant wheel pressure between slip rate and braking force gradient as estimated according to the present embodiment (which is converted into a gradient with respect to slip rate) agrees with true values. These true values were obtained by approximating a relationship between slip rate and braking force for step increases in wheel pressure using a brush model in which load movement is taken into consideration, and calculating the braking force gradient from this approximation model.

First, a description is given of the brush model in which load movement is considered.

Figure 8:
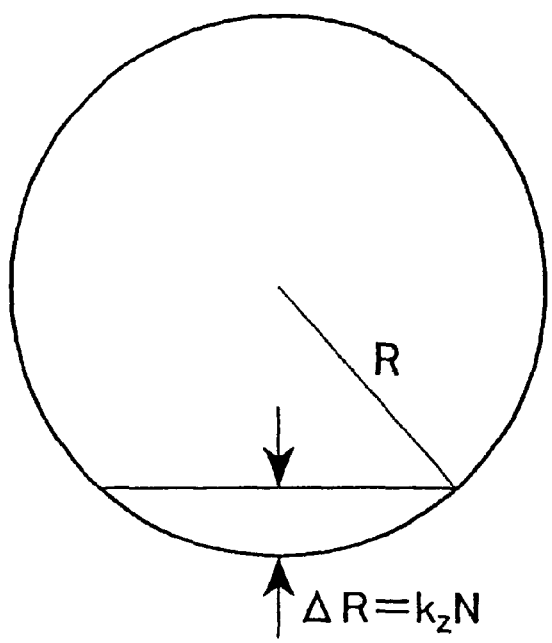
FIG. 8 illustrates displacement of a tire.

If it is assumed that tire displacement ΔR is proportionate to load N as shown in FIG. 8 (ΔR=$k_z$N), brake stiffness $K_S$ is proportionate to the load N as shown below.

$$K_S = k_{SO}N \quad (9)$$

Here, a braking force $F_x$ and a lateral force $F_y$ are expressed as follows.

$$F_x = \mu N \cos(1-\zeta_\epsilon^3)$$

$$F_y = \mu N \sin(1-\zeta_\epsilon^3) \quad (10)$$

and $$\zeta_s = 1 - \kappa k_{SO}/(3\mu) \quad (11)$$

where κ represents a combined slip.

Here, $\mu$ is a friction coefficient of the road surface. If it is assumed that $\kappa_x$, $\kappa_y$ and tan θ represent a longitudinal direction slip, a lateral slip, and a direction of slip, respectively, these are in relationships as shown below.

$$\kappa = \sqrt{(\kappa_x^2 + \kappa_y^2)}$$

$$\kappa_x = (u - R\omega)/(R\omega)$$

$$\kappa_y = K\beta v/(K_S R\omega)$$

$$\tan\theta = \kappa_x/\kappa_y$$

where R represents an effective radius of a tire, ω represents a wheel rotating speed (angular velocity), $\mu$ represents a longitudinal speed, v represents a lateral speed. If it is assumed that the load N increases in proportion to the lateral force F, i.e., that $N=N_0+k_N F_x$, the braking force and lateral force can be expressed as follows.

$$F_x = \mu N_0 \cos(1-\zeta_e^3)/(1-\mu k_N \cos(1-\zeta_e^3)) \qquad (12)$$

$$F_y = \mu N_0 \sin(1-\zeta_e^3)/(1-\mu k_N \cos(1-\zeta_e^3)) \qquad (13)$$

Figure 9:
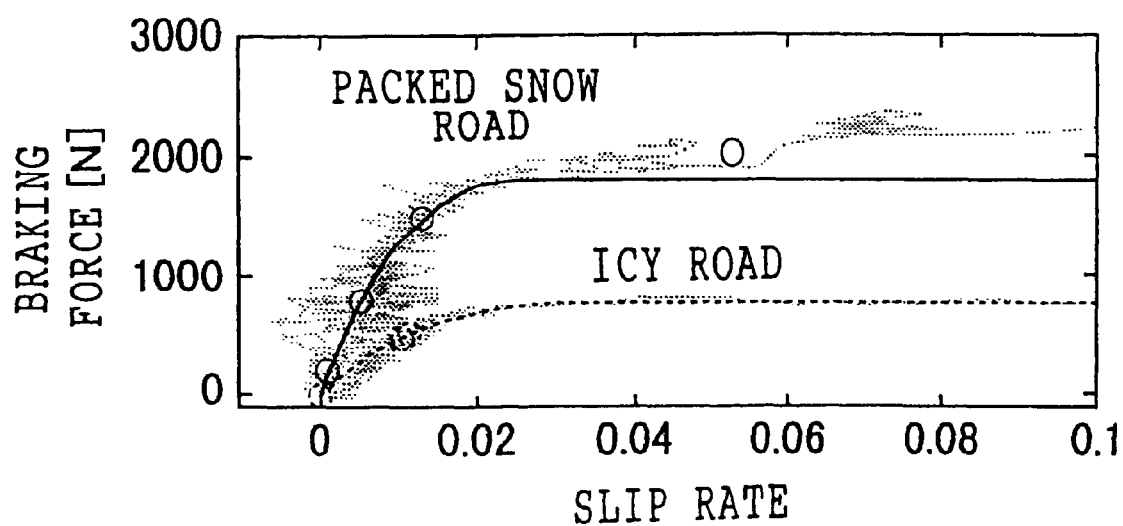
FIG. 9 is a diagram for comparing estimated values and actual values of braking force during forward braking.

FIG. 9 and FIG. 10 show relationships between slip rates and estimated braking forces and between slip rates and estimated braking force gradients (converted into and shown as gradients with respect to the slip rates) for braking with constant wheel pressure on a road covered with packed snow and on an icy road. Studless tires for a cold climate were used. All of the slip rates, estimated braking forces and braking force gradients are average values for five seconds after the beginning of braking. The true values indicated by broken lines were obtained by approximating the relationship between the slip rates and braking forces for step increases in the wheel pressures, using a brush model in which the load movement in Equation 12 is taken into consideration, and calculating gradients of the braking forces from this approximation model.

The break point frequency is identified from the wheel speed, the braking force gradient (gradient of braking force with respect to slip speed) is obtained from the identified break point frequency value using a map (the graph) in FIG. 7, is further multiplied with the wheel speed, and is shown as a braking force gradient with respect to slip rate.

It can be understood that an estimated value of the braking force gradient estimated according to the present embodiment agrees relatively well with the braking force gradient derived from the brush model, from the limit braking range where the braking force gradient is small to the low slip range where the braking force gradient is relatively large (near the origin).

A second embodiment of the present invention will now be described. In the present embodiment, a difference between a vibration level in a low frequency range and a vibration level in a high frequency range which is higher than the low frequency range, is used as a wheel speed frequency characteristic quantity so as to estimate road surface $\mu$ gradient.

As shown in FIG. 11, a wheel speed frequency characteristic quantity estimating section of the present embodiment is structured by: a low frequency characteristic quantity calculating section including a band-pass filter 40A for extracting a wheel speed signal in a low frequency range and a first vibration level calculating section 42A for calculating a vibration level from the wheel speed signal after filtering; a high frequency characteristic quantity calculating section including a band-pass filter 40B for extracting a wheel speed signal in a high frequency range and a second vibration level calculating section 42B for calculating a vibration level from the wheel speed signal after filtering; and a characteristic quantity calculating section 44 for outputting a difference between a low frequency characteristic quantity calculated by the low frequency characteristic quantity calculating section and a high frequency characteristic quantity calculated by the high frequency characteristic quantity calculating section, to serve as the wheel speed frequency characteristic quantity. A road surface $\mu$ gradient estimating section (not shown in the drawings) which corresponds to the braking force gradient estimating section 34 of the first embodiment is connected to the characteristic quantity calculating section 44.

The band-pass filter 40A of the low frequency characteristic quantity calculating section is set with a transmission frequency so as to transmit wheel speed signals in a region of relatively low frequency of wheel speed motion. The band-pass filter 40A in the present embodiment is set to transmit wheel speed signals at frequencies from 15 to 30 Hz. The band-pass filter 40B of the high frequency characteristic quantity calculating section is set with a transmission frequency so as to transmit wheel speed signals in a region of relatively high frequency of wheel speed motion. The band-pass filter 40B in the present embodiment is set to transmit wheel speed signals at frequencies from 30 to 50 Hz.

The first vibration level calculation (detection) section 42A squares the wheel speed signal transmitted by the band-pass filter 40A and outputs a signal indicating a vibration level in decibels to serve as the low frequency characteristic quantity. The second vibration level calculation (detection) section 42B squares a wheel speed signal transmitted by the band-pass filter 40B and outputs a signal indicating a vibration level in decibels to serve as the high frequency characteristic quantity.

The characteristic quantity calculating section 44 outputs a difference between the low frequency characteristic quantity and the high frequency characteristic quantity to serve as the wheel speed frequency characteristic quantity.

Figure 3:
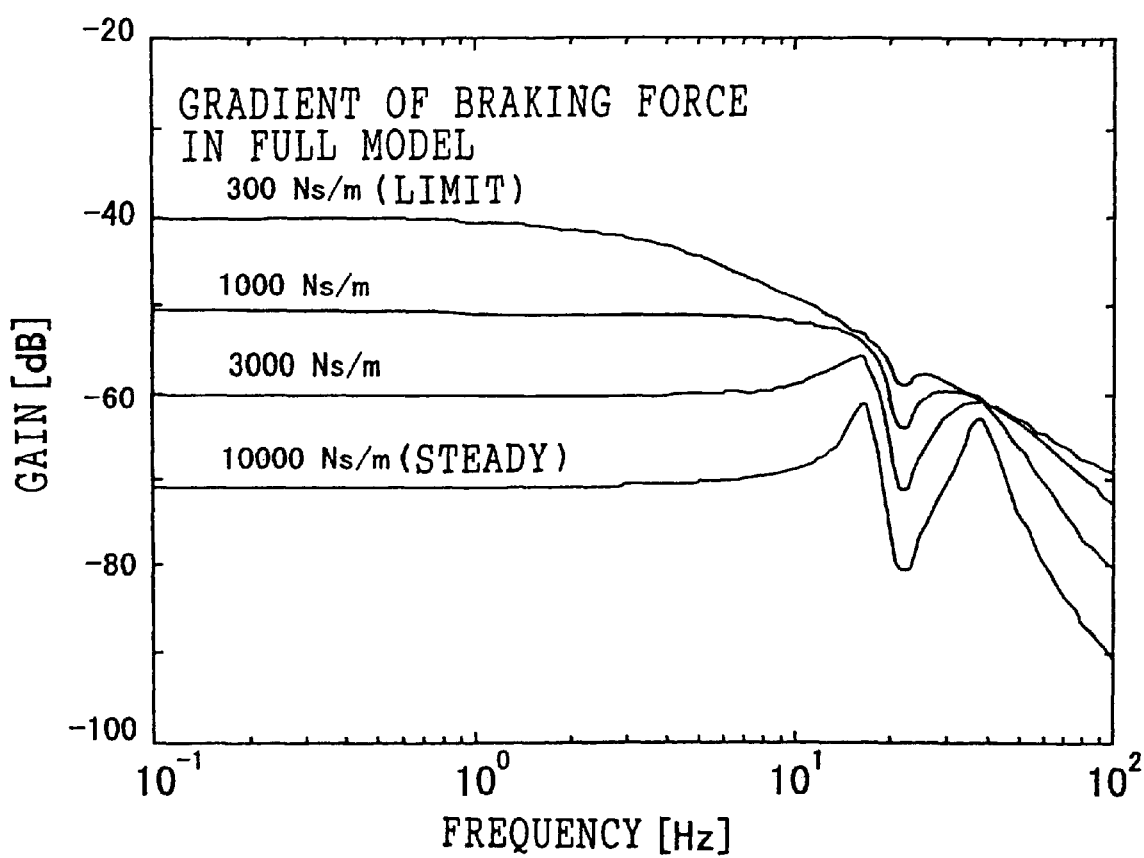
FIG. 3 is a gain diagram showing frequency responses from a road surface disturbance to the wheel speed.

As previously described with reference to FIG. 3, in a case near the limit or the like, namely, the $\mu$-gradient of the road surface (equivalent to the braking force gradient in FIG. 3) is relatively small, the frequency characteristics of the wheel speed exhibit high gain in the low frequency range and low gain in the high frequency range. Therefore, the wheel speed frequency characteristic quantity indicating the difference between the gain in the low frequency range and the gain in the high frequency range is large. In contrast, in a case of steady travelling or the like, namely, the road surface $\mu$-gradient is relatively large, the frequency characteristics of the wheel speed signals exhibit that the gain in low frequency range is smaller than that for the region where the $\mu$-gradient of the road surface is relatively small. Further, gain in high frequency range does not so much smaller compared to that for the region where the road surface $\mu$-gradient is relatively small, for reasons such as the occurrence of rotational resonance of the tire. This leads to a small wheel speed frequency characteristic quantity. Therefore, the wheel speed frequency characteristic quantity indicating the difference between the vibration level in the low frequency range and the vibration level in the high frequency range decreases as the road surface $\mu$-gradient increases. The road surface $\mu$-gradient can be estimated from the wheel speed frequency characteristic quantity by utilizing this property.

In the present embodiment, the road surface $\mu$ gradient estimating section, by using the property in which the wheel speed frequency characteristic quantity decreases as the road surface $\mu$-gradient increases, stores in advance a map showing a relation ship between the wheel speed frequency characteristic quantity indicating the difference between the vibration level in the low frequency range and the vibration level in the high frequency range and the road surface $\mu$-gradient, and estimates the road surface $\mu$ gradient from the estimated wheel speed frequency characteristic quantity and the map.

A third embodiment of the present invention will now be described. In the present embodiment, vibration levels in a plurality of frequency ranges are used as wheel speed frequency characteristic quantities, and road surface $\mu$-gradient is estimated.

Figure 12:
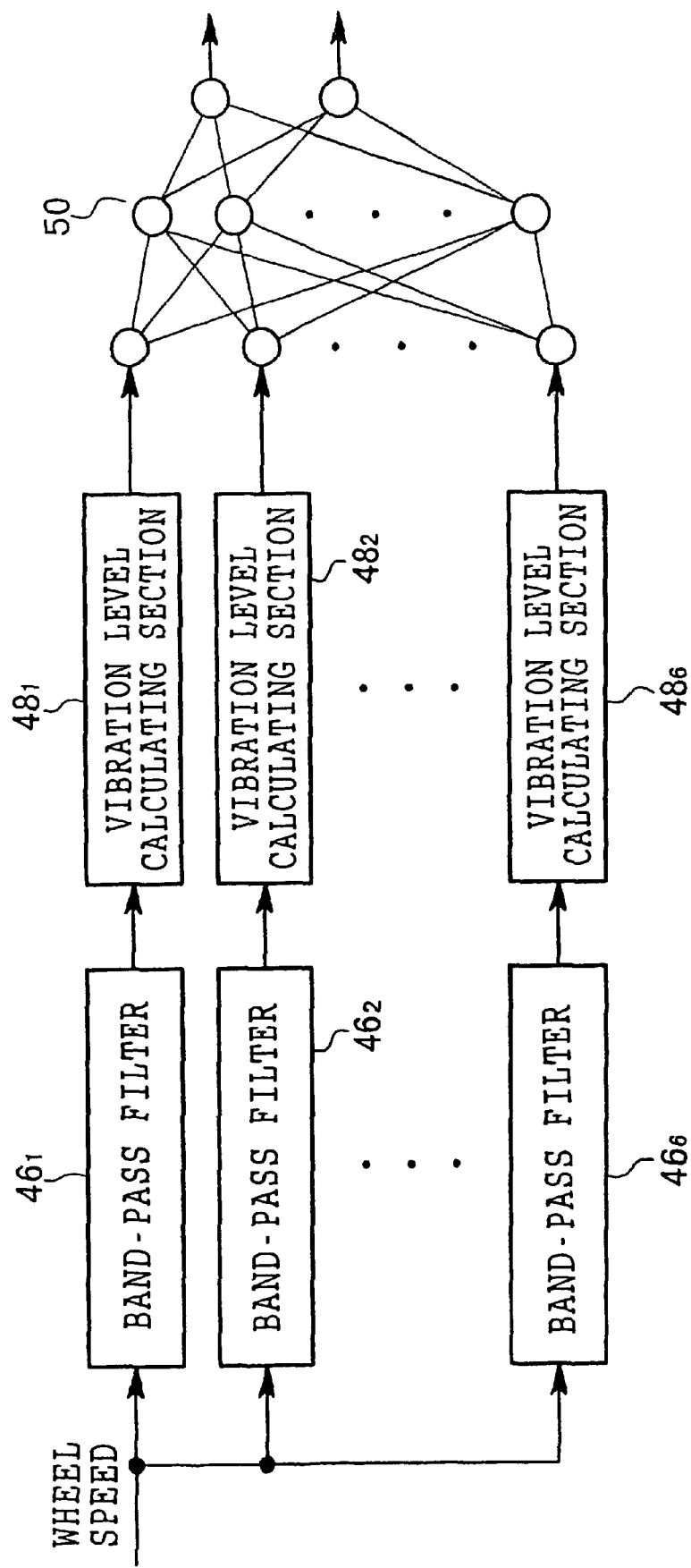
FIG. 12 is a block diagram showing a wheel speed frequency characteristic quantity estimating section of a third embodiment of the present invention.

As shown in FIG. 12, a wheel speed frequency characteristic quantity calculating section of the present embodiment has a plurality of band-pass filters $46_1, 46_2, \ldots, 46_6$ and a plurality of vibration level calculating sections $48_1, 48_2, \ldots, 48_6$ connected to the output ends of the band-pass filters. A road surface $\mu$-gradient estimating section 50 constituted by a neural network is connected to the plurality of vibration level calculating sections.

In the present embodiment, the characteristic quantity calculating section which is described in the second embodiment is connected to the wheel speed frequency characteristic quantity calculating section. In the present embodiment, the transmission frequency bands of the band-pass filters are six respective frequency bands of 10 to 20 Hz, 20 to 30 Hz, 30 to 40 Hz, 40 to 50 Hz, 50 to 60 Hz, and 60 to 70 Hz. The wheel speed frequency characteristic quantity calculating section outputs a vibration level for each of the plurality of frequency bands (six frequency bands) as the wheel speed frequency characteristic quantity. Although an example of using a band-pass filter for calculation of the vibration level for each frequency band is described for the present embodiment, the frequency components could be calculated using an FFT.

As described above, in the case of a small road surface $\mu$-gradient, gain falls off from a low frequency because the break point frequency of the wheel speed is low. In the case of a large road surface $\mu$-gradient, gain reduction does not occur until a high frequency because the break point frequency of the wheel speed is high. It is therefore possible to recognize an road surface $\mu$ gradient by comparing vibration levels in each frequency range.

The road surface $\mu$ gradient estimating section estimates a road surface $\mu$ gradient, from the vibration levels in the frequency bands as the wheel speed frequency characteristic quantities, by using the neural network and taking advantage of the fact that the break point frequency changes depending on the $\mu$-gradient of the road surface. The neural network has a three-layer configuration with an input layer, an intermediate layer, and an output layer. The network receives input of the six vibration levels and estimates three levels of the road surface $\mu$-gradient. Learning of the neural network is carried out with a back propagation method using frequency characteristics of wheel speed under three road surface $\mu$-gradients, i.e., high, middle and low road surface $\mu$-gradients. Thus, the neural network learns the property of increasing of the break point frequency when the road surface $\mu$-gradient increases, thus, capable of estimating a road surface $\mu$-gradient from the vibration levels in the frequency bands.

As described above, because a physical quantity which represents a road state, is estimated from a wheel speed frequency characteristic quantity which represents a following frequency of a transmission characteristics from a road disturbance to a wheel speed, the present invention is advantageous in that a physical quantity representing a road surface state in a low slip region including a steady travelling region can be estimated.

Also, because, in a transmission characteristics which is from a road surface disturbance to the wheel speed approximated to a low order model, a break point frequency in a gain diagram representing a frequency response of the approximated low order model, on the basis of time series data of a wheel speed, is estimated and a braking force gradient is estimated from the estimated break point frequency, the present invention is advantageous in that a physical quantity representing a road surface state in a low slip region including a steady travelling region can be estimated.

Also, because, on the basis of the wheel speed signal, a physical quantity as a wheel speed frequency characteristic quantity, for each of a plurality of frequency regions which are divided in a gain diagram representing a frequency response of transmission characteristics from a road surface disturbance to the wheel speed, is estimated, and a physical quantity that represents a road state, from the plurality of the estimated wheel speed frequency characteristic quantities is estimated, the present invention is advantageous in that a physical quantity representing a road surface state in a low slip region including a steady travelling (running) region can be estimated.

What is claimed is:

1. A road surface state estimating device comprising:
    a wheel speed sensor for detecting wheel speed and outputting a wheel speed signal;
    a wheel speed frequency characteristic quantity estimating section for estimating, on the basis of the wheel speed signal, a wheel speed frequency characteristic quantity that represents a difference between a characteristic quantity in a low frequency region and a characteristic quantity in a high frequency region that is higher than the low frequency region in a gain diagram representing a frequency response of transmission characteristics from a road surface disturbance to the wheel speed; and
    a physical quantity estimating section for estimating a physical quantity that represents a road state, from the estimated wheel speed frequency characteristic quantity.

2. A road surface state estimating device according to claim 1, wherein the physical quantity that represents the road state is a physical quantity that represents slipperiness between a tire and a road surface, including at least one of a braking force gradient, a driving force gradient and a road surface $\mu$ gradient.

3. A road surface state estimating device according to claim 1, wherein the characteristic quantity is a vibration level of the wheel speed signal.

4. A road surface state estimating device according to claim 1, wherein the wheel speed frequency characteristic quantity estimating section, comprises:
    a low frequency characteristic quantity calculating section for extracting a wheel speed signal in a low frequency range, the low frequency characteristic quantity calculating section comprising a first band-pass filter;
    a first vibration level calculating section for calculating a vibration level from the wheel speed signal after filtering;
    a high frequency characteristic quantity calculating section for extracting a wheel speed signal in a high frequency range, the high frequency characteristic quantity calculating section comprising a second band-pass filter;
    a second vibration level calculating section for calculating a vibration level from the wheel speed signal after filtering; and
    a characteristic quantity calculating section for outputting a difference between a low frequency characteristic quantity calculated by the low frequency characteristic quantity calculating section and a high frequency characteristic quantity calculating section, to serve as the wheel speed frequency characteristic quantity.

5. A road surface state estimating device comprising:
    a wheel speed sensor for detecting a wheel speed and outputting a wheel speed signal;
    a wheel speed frequency characteristic quantity estimating section for estimating, on the basis of the wheel speed signal, a wheel speed frequency characteristic quantity that represents, in a transmission characteristics, which is from a road surface disturbance to the wheel speed, approximated to a low order model, a frequency, at which gain changes from a value in a predetermined range to a value out of the predetermined range, in a gain diagram representing a frequency response of the approximated low order model; and a physical quantity estimating section for estimating a physical quantity that represents a road state, from the estimated wheel speed frequency characteristic quantity.

6. A road surface state estimating device according to claim 5, wherein the low order model is a first order lag model.

7. A road surface state estimating device according to claim 5, wherein the physical quantity that represents the road state is a physical quantity that represents slipperiness between a tire and a road surface, including at least one of a braking force gradient, a driving force gradient and a road surface $\mu$ gradient.

8. A road surface state estimating device comprising:

a wheel speed sensor for detecting wheel speed and outputting a wheel speed signal;

a wheel speed frequency characteristic quantity estimating section for estimating, on the basis of the wheel speed signal, a physical quantity as a wheel speed frequency characteristic quantity, for each of a plurality of frequency regions which are divided in a gain diagram representing a frequency response of transmission characteristics from a road surface disturbance to the wheel speed; and a physical quantity estimating section for estimating a physical quantity that represents a road state, from the plurality of the estimated wheel speed frequency characteristic quantities.

9. A road surface state estimating device according to claim 8, wherein the physical quantity that represents the road state is a physical quantity that represents slipperiness between a tire and a road surface, including at least one of a braking force gradient, a driving force gradient and a road surface $\mu$ gradient.

10. A road surface state estimating device according to claim 8, wherein the characteristic quantity is a vibration level of the wheel speed signal.

11. A road surface state estimating device according to claim 8, wherein the frequency regions include frequency bands of 10–20 Hz, 20–30 Hz, 30–40 Hz, 40–50 Hz, 50–60 Hz and 60–70 Hz.

12. A road surface state estimating device comprising:

a wheel speed sensor for detecting a wheel speed and outputting a wheel speed signal;

a wheel speed frequency characteristic quantity estimating section for estimating, on the basis of the wheel speed signal, a wheel speed frequency characteristic quantity which is based on each characteristic quantity of a respective plurality of frequency regions in a gain diagram representing a frequency response of transmission characteristics from a road surface disturbance to the wheel speed; and a physical quantity estimating section for estimating a physical quantity that represents a road state, from the estimated wheel speed frequency characteristic quantity.

13. A road surface state estimating device according to claim 12, wherein the plural frequency regions include a first frequency region that is a lower frequency region than a frequency region at which a tire rotation resonance is generated, and a second frequency region that is a higher frequency region than the first frequency region.

* * * * *